US009005156B2

(12) United States Patent
Nakamura

(10) Patent No.: US 9,005,156 B2
(45) Date of Patent: Apr. 14, 2015

(54) GAS MIST PRESSURE BATHING SYSTEM

(71) Applicant: ACP Japan Co., Ltd., Tokyo (JP)

(72) Inventor: Shoichi Nakamura, Nagano (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 6 days.

(21) Appl. No.: 14/125,763

(22) PCT Filed: Nov. 1, 2012

(86) PCT No.: PCT/JP2012/078311

§ 371 (c)(1),
(2) Date: Dec. 12, 2013

(87) PCT Pub. No.: WO2013/065777

PCT Pub. Date: May 10, 2013

(65) Prior Publication Data

US 2014/0107563 A1 Apr. 17, 2014

(30) Foreign Application Priority Data

Nov. 4, 2011 (JP) ................................ 2011-242315

(51) Int. Cl.

| | |
|---|---|
| ***A61M 37/00*** | (2006.01) |
| ***A61H 33/02*** | (2006.01) |
| ***A61H 33/14*** | (2006.01) |
| *A61H 33/06* | (2006.01) |

(52) U.S. Cl.

CPC ...... *A61H 33/028* (2013.01); *A61H 2201/1614* (2013.01); *A61H 33/14* (2013.01); (Continued)

(58) Field of Classification Search

CPC .................. A61H 2033/143; A61H 2033/145; A61H 2201/0157; A61H 2201/0207; A61H 2201/1614; A61H 2201/1619; A61H 2201/1623; A61H 2201/1635; A61H 2201/164; A61H 2201/165; A61H 33/028; A61H 33/14; A61H 33/10; A61H 35/00

USPC ........................................................... 604/24

See application file for complete search history.

(56) References Cited

U.S. PATENT DOCUMENTS

| | | | | |
|---|---|---|---|---|
| 4,792,097 A * | 12/1988 | Kremer et al. | ................ | 239/338 |
| 2010/0305497 A1* | 12/2010 | Tanaka et al. | .................. | 604/23 |

(Continued)

FOREIGN PATENT DOCUMENTS

| | | |
|---|---|---|
| JP | 2006-105284 A | 4/2006 |
| WO | 2012/099252 A1 | 7/2012 |

*Primary Examiner* — Jason Flick

(74) *Attorney, Agent, or Firm* — Manabu Kanesaka

(57) ABSTRACT

A gas mist pressure bathing system, which integrates a gas introduction part for increasing the supply pressure of a gas mist with a gas mist generator and enables the structure to be simplified and costs to be reduced, is provided. The gas mist pressure bathing system is provided with a gas supply means (10), a gas mist generating means (30), and a living body cover member (50). The gas mist generating means (30) is provided with, in an integrally formed manner: a connection part that connects to the gas supply means (10); a branched part that forces the gas flow from the connection part to branch off; a liquid storage part; a nozzle that discharges one of the gas flows that branched off at the branched part; a liquid-suctioning tube that transfers the liquid to the nozzle tip; a collision member that generates a gas mist by causing the liquid blown upwards by the gas flow discharged by the nozzle to collide; a merging part that merges the gas from above with the gas mist that was generated; a gas introduction part that guides the other gas flow that branched off at the branched part to the merging part; and a gas mist discharge part that collects and discharges the gas mist and gas that were generated.

20 Claims, 17 Drawing Sheets

(52) U.S. Cl.
CPC ..... *A61H2033/143* (2013.01); *A61H 2033/145* (2013.01); *A61H 2201/0157* (2013.01); *A61H 2201/0207* (2013.01); *A61H 2201/1619* (2013.01); *A61H 2201/1623* (2013.01); *A61H 2201/1635* (2013.01); *A61H 2201/164* (2013.01); *A61H 2201/165* (2013.01); *A61H 2201/5082* (2013.01); *A61H 2033/068* (2013.01)

(56) References Cited

U.S. PATENT DOCUMENTS

| | | | | |
|---|---|---|---|---|
| 2011/0060257 | A1 | 3/2011 | Nakamura | |
| 2011/0060258 | A1 * | 3/2011 | Nakamura | .................... 601/149 |
| 2011/0247610 | A1 | 10/2011 | Nakamura | |

* cited by examiner

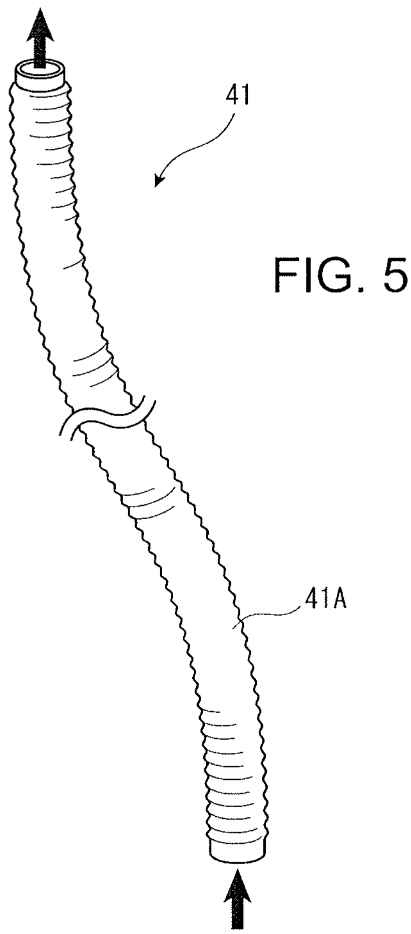
FIG. 5
FIG. 6
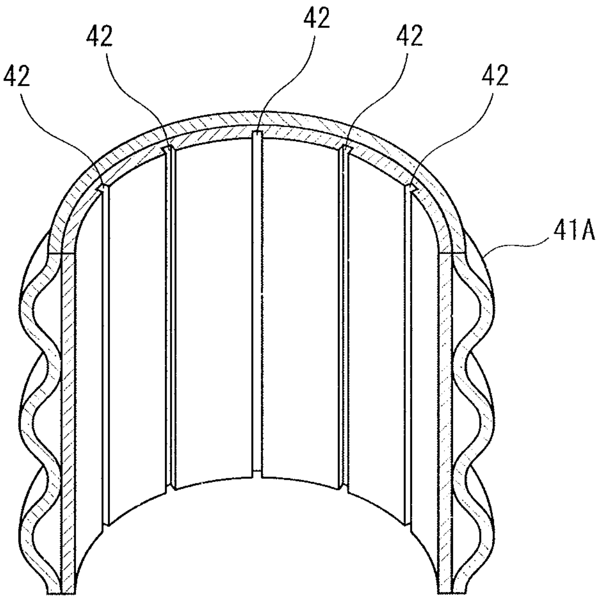

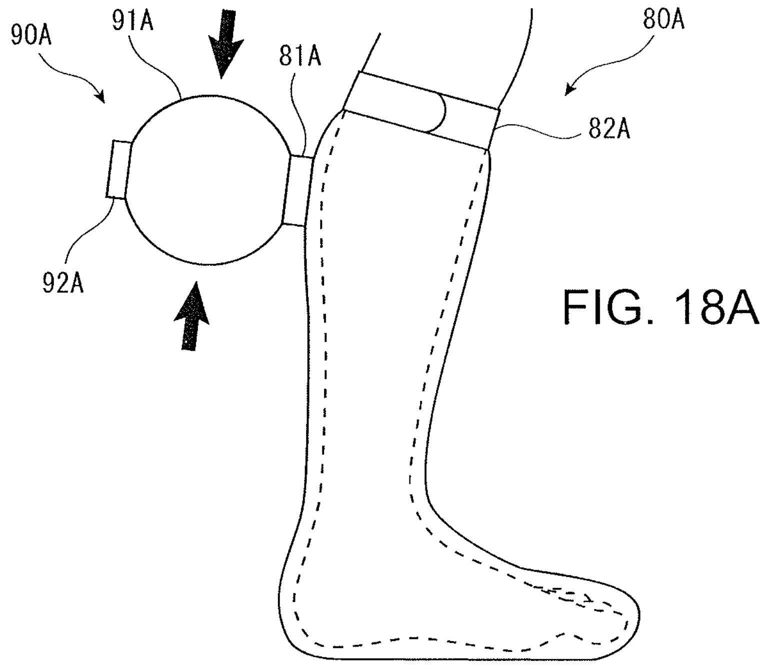
FIG. 18A
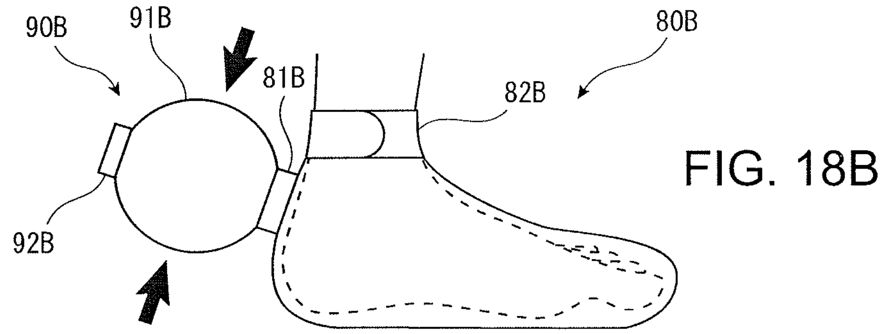
FIG. 18B
FIG. 18C
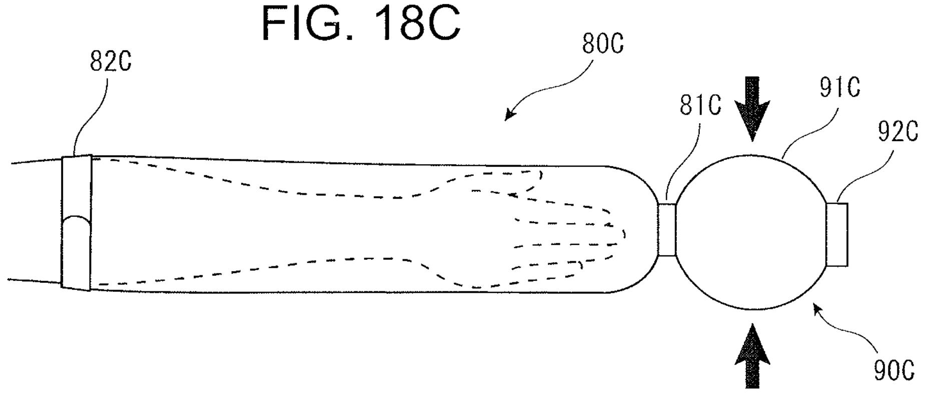

GAS MIST PRESSURE BATHING SYSTEM

RELATED APPLICATIONS

The present application is National Phase of International Application No. PCT/JP2012/078311 filed Nov. 1, 2012, and claims priority from Japanese Application No. 2011-242315, filed Nov. 4, 2011.

TECHNICAL FIELD

The present invention relates to a gas mist pressure bathing method and a gas mist pressure bathing system for improving absorption efficiency of gas into a skin or a mucous membrane of a living body, in which a gas mist is prepared by pulverizing liquid into micron sized mists dissolving oxygen or carbon dioxide, or a mixed gas of oxygen, carbon dioxide, and the gas mists are caused to directly contact the skin and mucous membrane of the living body at pressure of not less than a predetermined value.

BACKGROUND OF THE INVENTION

Conventionally, it has been known that carbon dioxide (carbonic acid anhydride: $CO_2$) has two properties of being not only soluble in water (water-soluble) but also soluble in fat (fat-soluble) and, owing to having both properties, when only contacting to the skin and the mucous membrane which are like as mixed with water and fat, carbon dioxide penetrates under a subcutaneous tissue and expands blood vessels around the penetrated parts, and it works to improve the blood circulation. By this action of accelerating the blood circulation, it displays various physiological effects such as dropping of blood pressure, improving of metabolism or accelerating to remove pain substance or waste product. Further, it has also anti-inflammation and anti-bacterial function. Therefore, carbon dioxide has recently been given attentions also from viewpoints of improving health or beauty other than the purpose of medical cares.

In the tissue of the living body, carbon dioxide works to release oxygen having been carried in combination with hemoglobin existing in a red blood cell. Around parts at the high concentration of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. Carbon dioxide seems to be waste products resulted from action of the cell, however, as is seen, it plays in fact very important roles in the living body.

Further, recently, oxygen of the high concentration has also widely been known as effective over activity of metabolism, acceleration of blood circulation, fatigue recovery, or stability of blood pressure. Other than them, oxygen has effects of disinfection or sterilization by oxidation.

Thereupon, an inventor of this invention has developed a gas mist pressure bathing system, in which oxygen or carbon dioxide is efficiently dissolved in a liquid and turned out into a mist for effectively giving a physiological action of oxygen or carbon to the living body. For example, he has before now proposed such a gas mist pressure bathing system, in which gas supplied in a gas mist generator is diverged into two groups, and one of them is used for generating the gas mist, while the other is supplied from the gas mist generator toward a discharge part, thereby to raise gas mist supplying pressure of the gas mist generator.

SUMMARY OF THE INVENTION

Problems that the Invention is to Solve

However, in the prior gas mist pressure bathing system, gas diverged within the gas mist generator was guided into a gas mist generation part through an outside attached tube. The case of using the outside attached tube took problems of requiring labor when setting up the system and increasing production cost. Further, if gas pressure was high, gas probably leaked out from tube connecting parts as tubes.

In view of the above mentioned circumstances, it is an object of the invention to provide such a gas mist pressure bathing system, in which a gas inlet for heightening supply pressure of the gas mist is integrated with the gas mist generator in order to simplify a structure and realize reduction in costs.

Means for Solving the Problems

For solving the above mentioned problems, the invention is to provide a gas mist pressure bathing system, which causes a mist (called as “gas mist” hereafter) to contact the skin or the mucous membrane of a living body, the mist having been prepared by pulverizing and dissolving carbon dioxide or oxygen and liquid, or a mixed gas (called as “gas” hereafter) of carbon dioxide and oxygen and liquid of concentration being not less than predetermined value, and the gas mist pressure bathing system comprising a gas supply means for supplying the above gas, a gas mist generation means for generating the gas mist of the gas supplied from the gas supply means and the liquid stored inside, and supplying the gas mist under a condition of mixing with the above gas, and a living body cover member for covering the skin and the mucous membrane of the living body and formed with a space for sealing inside the gas mist and gas supplied from the gas mist generation means, wherein the above mentioned gas mist generation means is integrally provided with a connection part to the gas supply means; a diverging portion of branching a gas flow from the connection part; a liquid storage of storing the liquid; a nozzle of discharging one-side gas flow branched by the diverging portion; a liquid suction pipe of sending the liquid to a front end of the nozzle; a collision member of generating the gas mist by colliding the liquid blown up by the gas flow discharged from the nozzle with this collision member; a confluent part of joining the generated gas mist with the gas from an upward side; a gas inlet of leading the other-side gas flow branched by the diverging portion until the confluent part; and a gas mist discharge part of collecting and discharging the generated gas mist and gas.

By the way, the invention refers it as “pulverizing and dissolving” to pulverize the liquid into fine liquid drops, and cause to contact and mix with gas (carbon dioxide or oxygen, or the mixed gas of carbon dioxide and oxygen).

Herein, with respect to the gas mist pressure bathing system of the invention, in the gas mist generation means, it is desirable that at least the liquid storage is made removable and exchangeable with another liquid storage.

Further, the gas mist pressure bathing system of the invention is desirably further provided with sensors for detecting measured values of air pressure, temperature, concentrations of oxygen and carbon dioxide, and moisture and others, and control means for controlling interior of the living body cover member based on the measured values of the sensors to be within ranges of the set values having been in advance determined.

It is also sufficient to further equip a pressurization means for pressurizing the interior of the living body cover member. By the way, this pressurization means communicates with the living body cover member, and desirably consists of a hollow gas storage enabling to discharge the gas mist into the living body cover member.

By supplying the gas mist intermittently into the living body cover member by the control means, the living body cover member may be effected with interval pressurization. Otherwise, if the pressurization member intermittently discharges the gas mist into the living body cover member, it is also sufficient to carry out the interval pressurization on the living body cover member.

Next, it is preferable that the above mentioned liquid is any one or plural combination of water, ionic water, ozone water, physiological salt solution, purified water, or sterilized and purified water. And it is desirable to further contain any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, citric acid, ethanol, chlorhexidine gluconate, amphoteric surface active agent, benzalkonium chloride, alkyl diamino etherglycine acetate, sodium hypochlorite, peracetic acid, sodium sesqui-carbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

A size of the mist supplied from the gas mist generation means into the living body cover member is suitably not larger than 10 μm.

The control means preferably holds pressure at 1.01 to 1.4 air pressure within the living body cover member when taking the gas mist pressure bathing.

Further on, there may be provided an electric charge giving means for giving an electric charge to the mist supplied by the gas mist generation means. At this time, the electric charge is preferably minus.

Desirably, the gas mist generation means has a gas mist supply pipe for supplying the gas mist and gas into the living body cover, and this gas mist supply pipe is furnished with a filter for removing liquid drops attaching to the inside of the pipe. Still further, the gas mist supply pipe is suitably composed of a cornice shaped pipe over a whole or at one part of the gas mist supply pipe. The cornice shaped pipe is suitably formed inside with a groove in an axial direction of the pipe. In addition, this gas mist supply pipe is provided with a check valve.

The living body cover member is also desirably furnished with the check valve at the gas mist supply port. By the way, it is suitable that the control means stops the gas supply from the gas supply means when the pressure value becomes more than the predetermined value.

Preferably, the gas mist generation means is in advance sterilized.

Effects of the Invention

According to the gas mist pressure bathing system of the invention, by making the gas inlet for heightening pressure of supplying the gas mist integrate with the gas mist generator, the structure of the invention is simplified to curtail using labors, enabling to reduce production cost and also avoid gas leakage.

BRIEF DESCRIPTION OF THE DRAWINGS

FIG. 5 Atypical view showing an example of the gas mist supply pipe of connecting the gas mist generator and the living body cover of the invention;

FIG. 6 A perspective view in cross section of the gas mist supply pipe shown in FIG. 5;

FIGS. 18A-18C Typical views showing configuration examples (No. 1) of the living body cover in the gas mist pressure bathing system in dependence on the second embodiment of the invention;

EMBODIMENTS FOR PRACTICING THE INVENTION

In the following description, explanations will be made to embodiments of this invention, referring to the attached drawings.

First Embodiment

Figure 1:
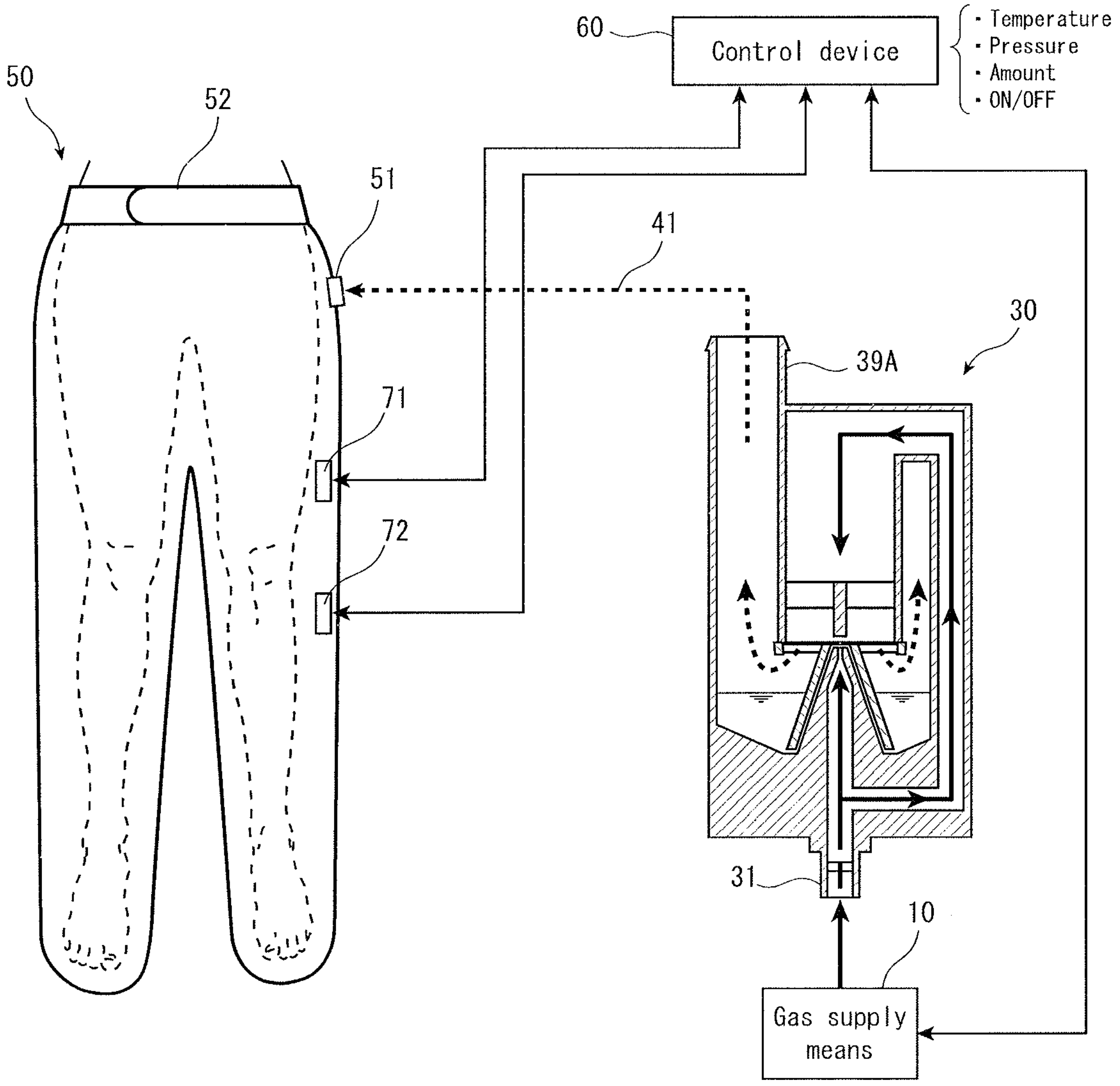
FIG. 1 A generally schematic view of the gas mist pressure bathing system in dependence on the first embodiment of the invention.

FIG. 1 is the generally schematic view of the gas mist pressure bathing system in dependence on the first embodiment of this invention. As shown in FIG. 1, the gas mist pressure bathing system of the present embodiment comprises a gas supply means 10 for supplying oxygen, carbon dioxide, or the mixed gas (called briefly as "gas" hereafter) of oxygen and carbon dioxide, a gas mist generator 30 serving as a gas mist generation means, and a living body cover 50 serving as a living body cover member for sealing inside the supplied gas mist and gas. Further, a control device 60 is preferably furnished as a control means.

The gas supply means 10 supplies gas to a later mentioned connection part 31 of the gas mist generator 30. For example, a gas bomb of a cartridge system, a cassette gas bomb or a compressed-gas container for official uses are also sufficient. The gas supply means 10 may be attached with a regulator for adjusting gas pressure, though not showing. It is also enough to dispose a gas heating heater and a temperature controlling gauge.

The gas mist generator 30 previously stores inside the liquid, generates the gas mist by pulverizing and dissolving the liquid and gas by high speed flowing of gas supplied from the gas supply means 10, further mixes gas, and supplies the gas mist into the living body cover 50.

Figure 2:
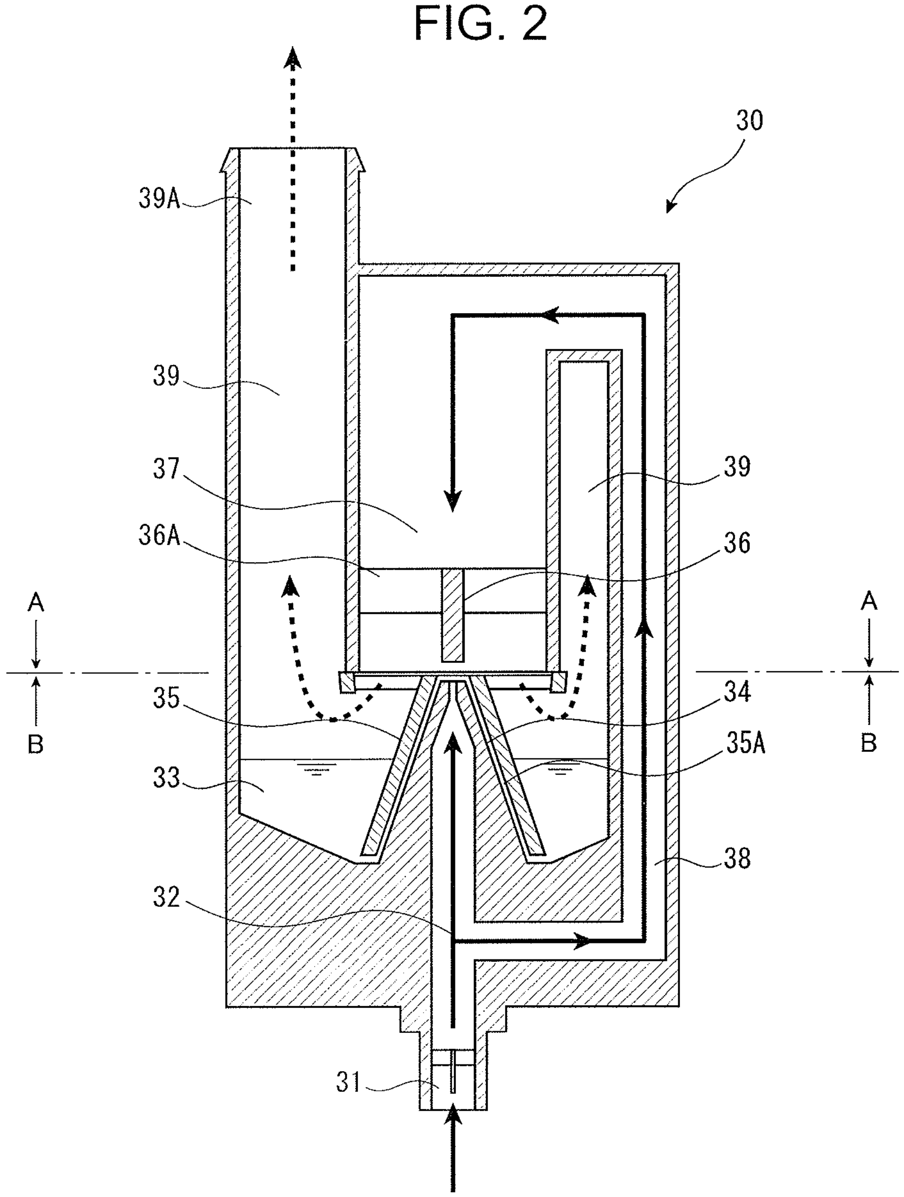
FIG. 2 A typical view in cross section showing the structure of the gas mist generator in the gas mist pressure bathing system of FIG. 1.
Figure 3:
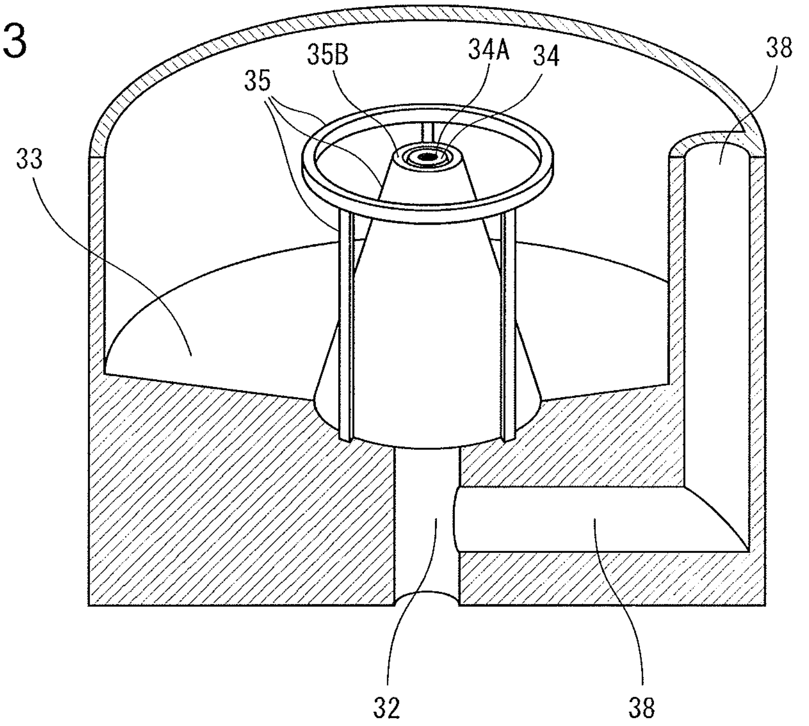
FIG. 3 A perspective view in cross section of the gas mist generator, seeing from an arrow A direction of FIG. 2.
Figure 4:
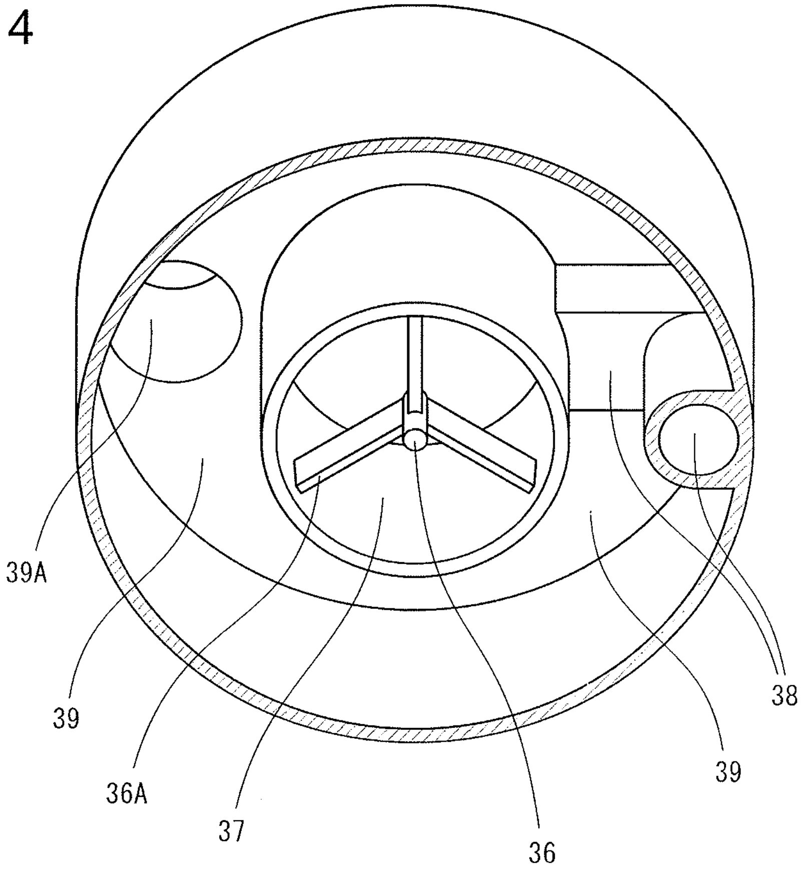
FIG. 4 A perspective view in cross section of the gas mist generator, seeing from an arrow B direction of FIG. 2.

FIG. 2 is the typical view in cross sectional showing the structure of the gas mist generator 30. FIG. 3 is the perspective view in cross section of the gas mist generator 30 seeing from an arrow A direction of FIG. 2. By the way, FIG. 3 omits a wall part and the connection part 31 in the front side of a liquid storage 33. FIG. 4 is the perspective view in cross section of the gas mist generator, seeing from the arrow B direction of FIG. 2.

As showing in these Figures, the gas mist generator 30 comprises the connection part 31 connected to the gas supply means 10, a diverging portion 32 for branching the gas flowing from the connection part 31, a liquid storage 33 of storing the liquid, a nozzle 34 of discharging one-side gas flow branched by the diverging portion 32, a liquid suction pipe 35A of sending the liquid to the front end of the nozzle 34, a baffle (collision member) 36 of colliding the liquid blown up by the gas flow discharged from the nozzle with this baffle, a confluent part 37 of joining the generated gas mist with gas from an upward side, a gas inlet 38 of leading the other side gas flow branched by the diverging portion 32 until the confluent part 37, and a gas mist discharge part 39 of collecting and discharging the generated gas mist, and those members are formed integrally as one body.

To the connection part 31, the gas supply means 10 is connected directly, or via a gas code. The connection part 31 has such as a structure enabling to connect, by one touch, the gas supply means 10 or a gas code connected to the gas supply means 10, and in accordance with the gas supply means 10 to be connected, various forms may be employed.

Gas supplied from the gas supply means 10 via the connection part 31 is branched into two routes at the diverging portion 32. One of them directs to the nozzle 34, while the other to the gas inlet 38. Gas having directed to the nozzle 34 is discharged out of a front end open 34A of the nozzle. On the other hand, gas directing to the gas inlet 38 is guided to the confluent part 37.

The liquid storage 33 has been stored and sealed with a predetermined liquid in advance when having built at a stage of setting up the system of this invention. When using, this liquid storage is opened to perform the gas mist pressure bathing. Herein, as the liquid stored in the liquid storage 33, it is preferable to employ water, ionic water, ozone water physiological salt solution, purified water or sterilized and purified water. Further, these liquids are sufficient to contain medicines useful to users' diseases or symptom. As the medicines, for example, listed are anti-allergic agent, anti-inflammatory agent, anti-febrile agent, anti-fungus agent, anti-influenza virus agent, influenza vaccine, steroid agent, anti-cancer agent, or anti-hypertensive agent, cosmetic, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic agent moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Otherwise, the liquid may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate. In addition, carbonate spring of high concentration may be added (examples of organic components are sulfate, carbonate, or sodium dichloroiso-cyanurate).

At the bottom center of the liquid storage 33, the nozzle 34 is placed. This nozzle 34 protrudes from the bottom of the liquid storage 33, and is squeezed in diameter toward the baffle 36 to be formed almost as a circular cone. The nozzle 34 is connected, at its base end, to one side of the diverging portion 32, and the nozzle 34 enables to discharge gas from its front end open 34A.

The liquid suction pipe 35A is formed between the outer circumference of the nozzle 34 and a liquid suction pipe-forming member 35 shaped in the almost circular cone being larger by one turn than the nozzle 34. That is, as shown in FIG. 2, by positioning as covering the liquid suction pipe-forming member 35 over the nozzle 34, a liquid suction pipe 35A is defined between the outer circumference of the nozzle 34 and the inner circumference of the liquid suction pipe-forming member 35. Although having omitted to show, since a minute nail shaped projection is provided at a base end (the lower part of the almost circular cone part) of the liquid suction pipe-forming member 35, a space is defined on the bottom between a base of the liquid suction pipe-forming member 35 and the bottom of the liquid storage 33, and from this space the liquid stored in the liquid storage 33 is sucked up by the liquid suction pipe 35A. In addition, the front end 35B of the liquid suction pipe-forming member 35 opens nearly the front end opening 34A of the nozzle 34, and the liquid sucked up by the liquid suction pipe 35A collides with the gas flow discharged from the nozzle 34.

The liquid sucked up by the liquid suction pipe 35A collides with the gas flow discharged from the nozzle 34 and is blown up, struck against the baffle 36 placed in opposition to the front end open 34A of the nozzle 34 and crashed to turn out the gas mist. Herein, the baffle 36 is fixed to the inside wall of the confluent part 37 by a baffle supporter 36A, but may be fixed to a liquid suction pipe-forming member 35.

On the other hand, gas branched at the diverging portion 32 into the gas inlet 38 gets to the confluent part 37 following the gas inlet 38. The gas inlet 38 is such a guiding path which passes the side face of the inside of the gas mist generator 30 from the diverging portion 32 equipped at the lower part of the gas mist generator 30 and goes toward an upper part, and this gas inlet 38 is formed integrally in the gas mist generator 30. The confluent part 37 is made of a cylindrical member disposed as encircling the baffle 36 above the front end open 34A of the nozzle 34, and communicates with the gas inlet 38. Accordingly, gas branched at the diverging portion 32 and guided to the gas inlet 38 confluents with the gas mist generated in the confluent part 37 at the upper part, and pushes out the gas mist toward a gas mist discharge part 39 formed around the cylindrical confluent part 37.

Gas supplied from the gas inlet 38 into the confluent part 37 can control supply pressure owing to the size of a diameter of the gas inlet 38. By controlling gas supply pressure, the gas mist supplying amount of the gas mist generator 30 is also can be controlled. Further, concentration of the gas mist (mist concentration in gas) or grain sizes of the mist can be also controlled by the diameter size of the gas inlet 38.

A gas mist discharge part 39 is a space formed around the cylindrical confluent part 37, collecting the gas mist driven out from the confluent part 37 by gas coming from the gas inlet 38 and discharging the gas mist together with gas. The gas mist driven out into the gas mist discharge part 39 is discharged into the living body cover 50 from the gas mist discharge port 39A opening at the upper part of the gas mist generator 30. An interval between the gas mist discharge port 39A and the living body cover 50 is connected by a gas mist supply pipe 41.

The gas mist generator 30 may be made such a structure which is able to displace a region including at least the liquid storage 33 and to replace another new liquid storage 33. That is, the gas mist generator 30 is made an assembling system and a replacing part including the liquid storage 33 is set up with another region, thereby enabling to accomplish the gas mist generator 30 integrating with the gas inlet 38. Thus, if making the liquid storage 33 replaceable, the liquid storage 33 may be disposable enabling to keep hygiene. By making the liquid storage 33 replaceable, it is possible to omit a structure of supplementing the liquid into a liquid suction pipe 35A and to realize a device to be compact.

By the way, the above mentioned gas mist generator 30 is desirably in advance treated with sterilization when having built at a stage of setting up the system of this invention.

The gas mist supply pipe 41 is desirably composed wholly or partially with a soft and cornice shaped pipe 41A of large diameter as shown in FIG. 5, and this is freely bent or expanded and contracted so that a user's action is not limited. In addition, as shown in FIG. 6, the cornice shaped pipe 41A is formed inside with grooves 42 in an axial direction of the pipe. By thus forming the grooves 42 inside of the pipe 41A, when the gas mist flowing within the gas mist supply pipe 41 is liquefied, the droplet is easily collected and recovered. FIG. 6 illustrates the inside of the cornice shaped pipe 41A to be smooth, but may be formed to be cornice shape as the outside. Also in such a case, by forming the grooves 42, the liquefied gas mist is recovered.

The gas mist supply pipe 41 is provided inside with a check valve to avoid back flows of the gas mist and gas. Further, though not showing, the gas mist supply pipe 41 is preferably provided with a droplet removing filter to remove extra droplets attaching to the inside of the pipe.

The living body cover 50 enables to form a space for covering the skin and mucous membrane of the living body (herein, as the example, the lower extremity of the living body) and to seal the gas mist and gas inside. As an example, FIG. 1 shows a shape as trousers covering the lower extremity of the living body. The living body cover 50 is composed of a pressure resistant, non-air permeable and non-moisture permeable material, for example, preferably, the natural rubber, silicone rubber, polyethylene, polypropylene, polyvinylidene chloride, polystylene, polyvinyl acetate, polyvinyl chloride, polyamide resin, polytetrafluoroethylene, and a multi-layer structure of these raw materials is sufficient.

The living body cover 50 is connected to the gas mist supply pipe 41 and has the supply port 51 for introducing the gas mist and gas inside. The supply port 51 is provided inside with the check valve to prevent from back-flow of the gas mist and gas. The living body cover 50 have an open or a valve enabling to discharge the gas mist and gas for controlling inside pressure. Pressure control may be performed manually, but is desirably automatically based on measuring values of a later mentioned manometer 71 by a control device 60 together with supply or control of the gas mist. Further, a safety valve (by-pass valve) may be provided for automatically opening the valve when the inside of the living body cover 50 becomes more than a fixed pressure.

The living body cover 50 is inside installed with a manometer 71 for measuring internal pressure. The control device 60 controls generation or supply of the gas mist on the basis of measuring values of the manometer 71 for maintaining a pressure value within the living body cover 50 to be more than 1 air pressure (more preferably, around 1.01 to 1.4 air pressure). For example, supply of gas from the gas supply means 10 is controlled or stopped, otherwise, the gas mist from the living body cover 50 is discharged. Further, the living body cover 50 is inside installed with a temperature gauge 72 for measuring temperature within the living body cover 50. The control device 60 performs "on-off" of a heater installed in the gas supply means 10 on the basis of measuring values of the temperature gauge 72 for maintaining a determined temperature (for example, around 38° C.) bringing about warm bath effects within the living body cover 50. As to others, the living body cover 50 may be installed inside with sensors for measuring concentrations of oxygen and carbon dioxide, moisture and others for controlling interiors of the cover based on the measured values to be within ranges of predetermined values by the control 60.

The living body cover 50 has, around its opening, a stopper 52 for attaching to and detaching from the living body (herein, the lower extremity of the living body) and for preventing leakage of the gas mist. The stopper 52 is suitably composed of, e.g., a face fastener of stretching property, or may have a sole string, rubber or their combination. For heightening a sealing property of the living body cover 50, the inside (such as an inside of the stopper 52) thereof may have a material attaching to the user's skin. The adhesive material is preferably, for example, a visco-elastic gel made of poly-urethane or silicone rubber. Further this adhesive material is detachably used and exchangeable each time or if viscosity becomes weak.

The control device 60 is composed of a computer having CPU, memory and display. Pressure control, on-off switch of gas supplied from the gas supply means 10 or on-off switch of supply of the gas mist are performed for taking the gas mist pressure bathing under the optimum condition. In particular, such a structure is desirable that, when the pressure value within the living body cover 50 becomes more than a predetermined value, the structure stops supplying gas from the gas supply means 10 by the control device 60. By the way, the above mentioned adjustment may be manual, not using the control device 60.

Next, reference will be made to one example of sequences taking the gas mist bathing by use of the gas mist pressure bathing system of the above mentioned first embodiment.

Firstly, the sealed gas mist generator 30 is unsealed and connected to the gas supply means 10. The living body cover 50 is secured to the living body (herein, the lower extremity of the living body) and sealed. The gas starts to supply from the gas supply means 10 to the gas mist generator 30.

Figure 7:
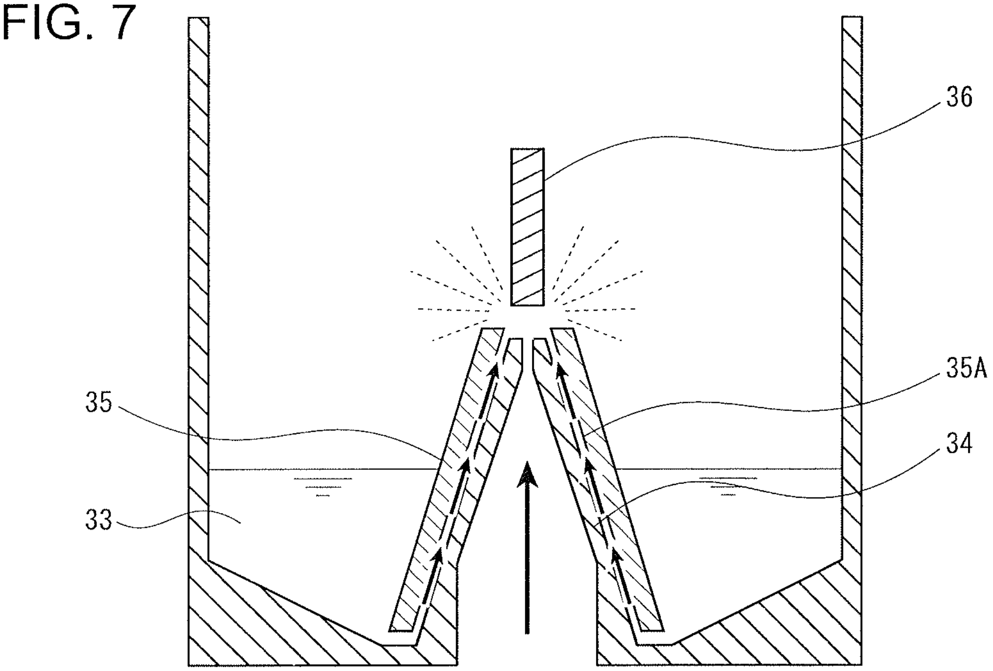
FIG. 7 A partially enlarged cross sectional view of the gas mist generator in the gas mist pressure bathing system in FIG. 1.

When gas is supplied into the nozzle 34, since the nozzle 34 is reduced in diameter toward the front end as shown in FIG. 7, gas heightens the flowing speed and is discharged. The liquid in the liquid storage 33 is sucked up within the liquid suction pipe 35A owing to negative pressure caused by air flow of this time, is blown up by gas at the front end portion 35B of the liquid suction pipe 35A, and collides against the baffle 36, so that the gas mist is generated. Desirably, the diameter of the mist generated by this collision is fine, and concretely, best is not larger than 10 μm. The thus finely pulverized mist can display effects of minus ion.

The gas further passes through the diverging portion 32 and is guided to the confluent part 37 from the gas inlet 38, and heightens discharging pressure of the generated gas mist. The generated gas mist is mixed with gas from the diverging portion 32 and discharged from the gas mist discharge port 39A into the living body cover 50 via the gas mist supply pipe 41. From measuring values of a manometer 71 and temperature gauge 72, the control device 60 adjusts each of the means so that the inside of the living body cover 50 is kept to be optimum conditions of pressure and heating temperature (around 1.01 to 1.4 air pressure, and around 38° C.), and under these conditions, the gas mist pressure bathing is taken.

The above mentioned explanation has been made to the lower extremities of the human living body as the example to be performed with the pressure gas mist bathing, and the invention is applicable to various parts of the living body. Then, the optimum pressure gas mist bathing is performed by using the shapes of the living body cover 50 meeting objective parts of the living body.

Figure 8:
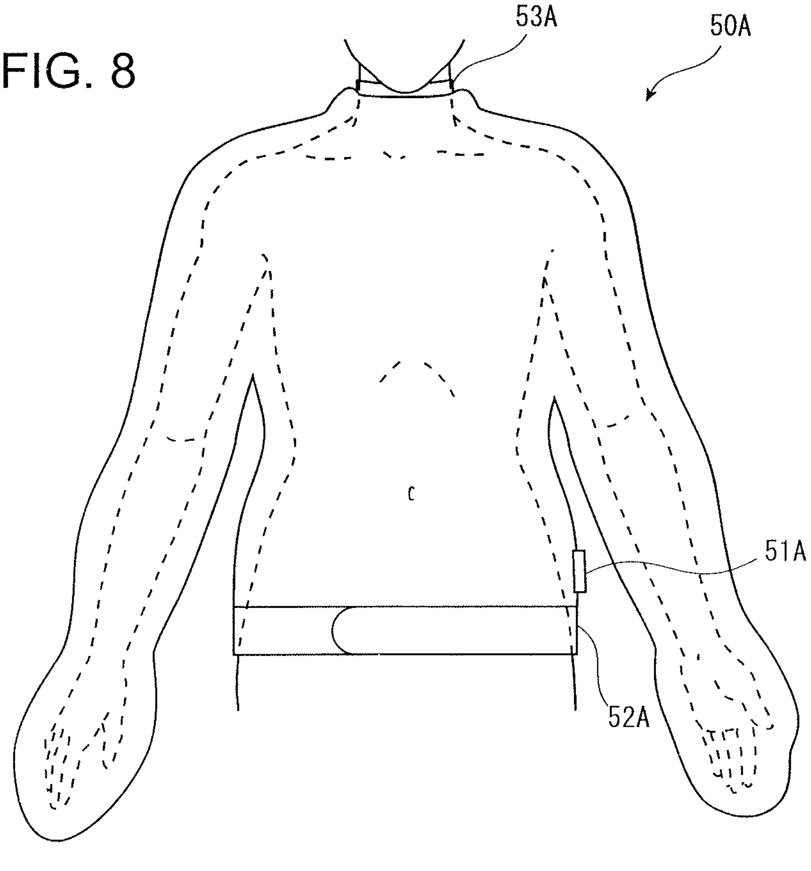
FIG. 8 A typical view showing a configuration example (No. 1) of the living body cover in the gas mist pressure bathing system in dependence on the first embodiment of the invention.

FIGS. 8 to 10 show the various shaped examples of the living body cover 50. At first, FIG. 8 shows the schematic view of the living body cover 50A for the upper half of the living body. The living body cover 50A has a shape for wrapping the whole of the upper half of the living body, and has a stopper 52A for attaching to and detaching from the living body when opening a waist part and stopping leakage of the gas mist sealed inside. A stopper 53A is similarly formed around the opening of a neck. 51A designates a supply port for introducing inside the gas mist.

Figure 9A:
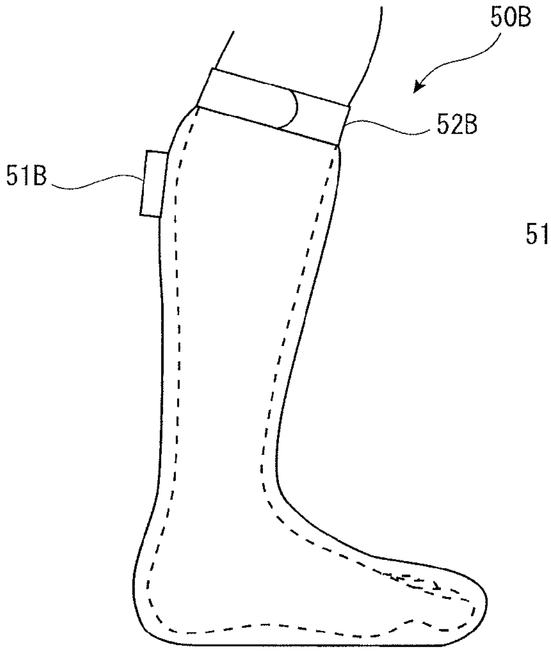
FIGS. 9A-9E Typical views showing configuration examples (No. 2) of the living body cover in the gas mist pressure bathing system in dependence on the first embodiment of the invention.
Figure 9B:
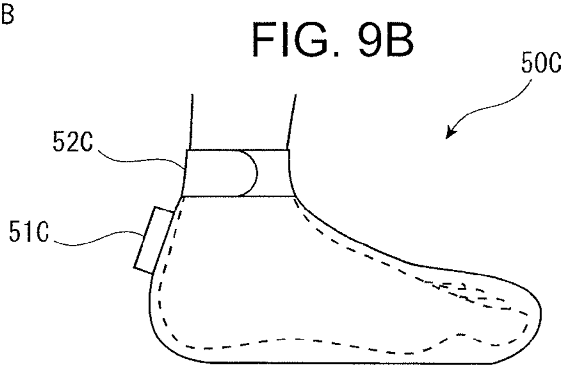
Figure 9C:
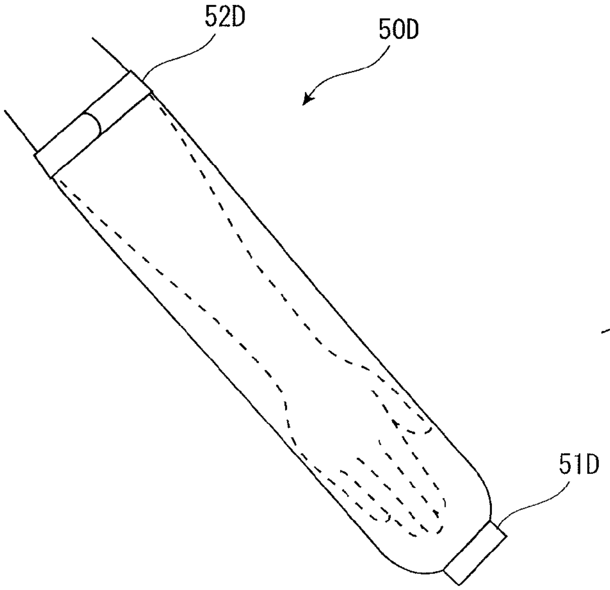
Figure 9D:
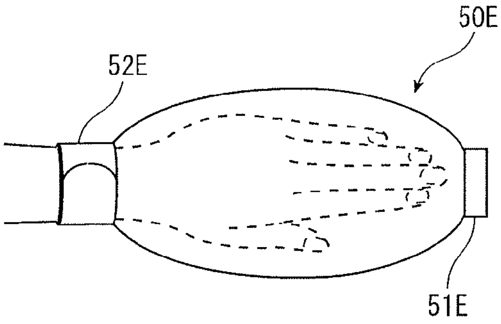
Figure 9E:
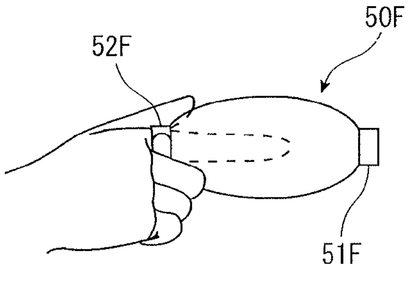

FIGS. 9A to 9E show the variously shaped examples of the living body cover 50 for covering more locally limited parts of the living body. FIG. 9A is a living body cover 50B for one-side lower extremity (lower part under a knee) of the living body. This living body cover 50B has a stopper 52B at its opening part and a supply port 51B for introducing inside the gas mist and gas. FIG. 9B is a living body cover 50C for a foot. The living body cover 50C has a stopper 52C at its opening part and a supply port 51C for introducing inside the gas mist and gas. FIG. 9C is a living body cover 50D for a forearm. The living body cover 50D has a stopper 52D at its opening part and a supply port 51D for introducing inside the gas mist and gas. FIG. 9D is a living body cover 50E for a hand of the living body. The living body cover 50E has a stopper 52E at its opening part and a supply port 51E for introducing the gas mist and gas inside thereof. FIG. 9E is a living body cover 50F for fingers of the living body. The living body cover 50F has a stopper 52F at its opening part and a supply port 51F for introducing the gas mist and gas inside thereof.

Figure 10A:
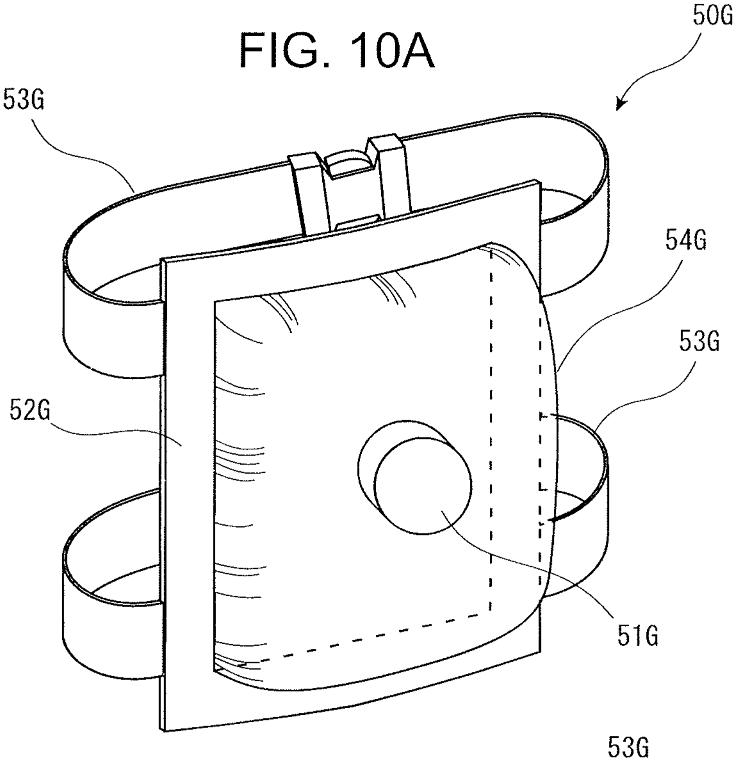
FIGS. 10A-10B Typical views showing configuration example (No. 3) of the living body cover in the gas mist pressure bathing system in dependence on the first embodiment of the invention.
Figure 10B:
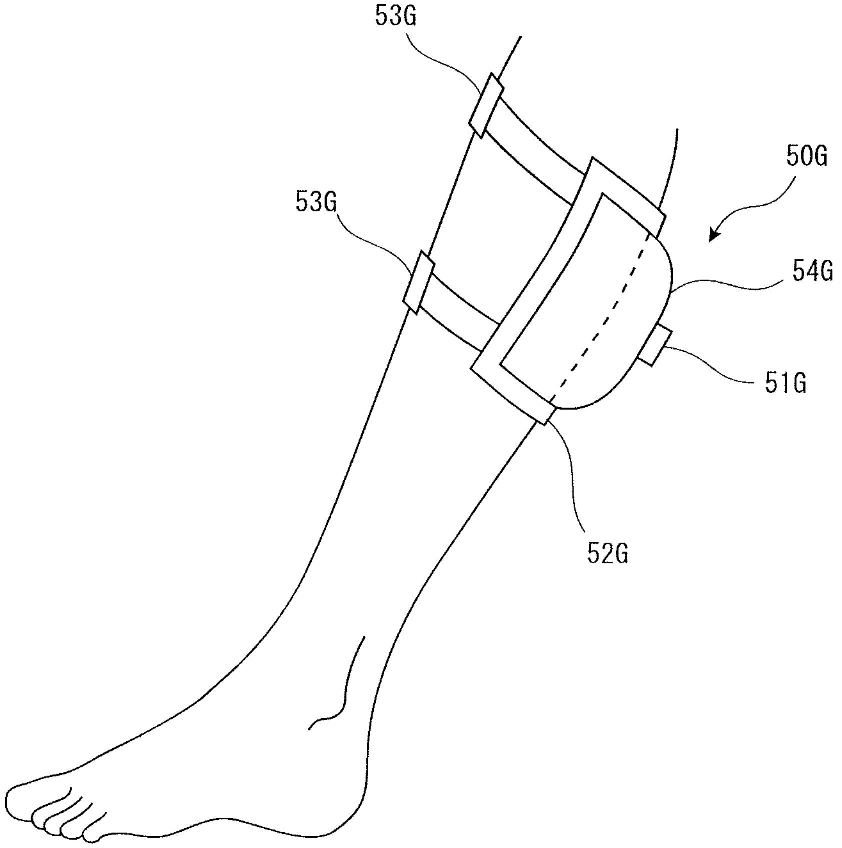

FIGS. 10A and 10B show examples of a patch shaped living body cover 50G. FIG. 10A is a view showing the outline of the patch shaped living body cover 50G. FIG. 10B is a view showing an outline of the patch shaped living body cover 50G. FIG. 10B is a view showing an external appearance when attaching the patch shaped living body cover 50G to the living body (herein, the lower extremity). The living body cover 50G is composed of a cover part 54G for covering the skin and mucous membrane of the living body, a stopper 52G provided at the margin of the cover part 54G and directly attached to the skin and mucous membrane, fasteners 53G made of belts or strings for fastening the cover part 54G to the living body, and a supply port 51G for supplying the gas mist and gas into the space defined by the cover part 54G and the stopper 52G.

Figure 11:
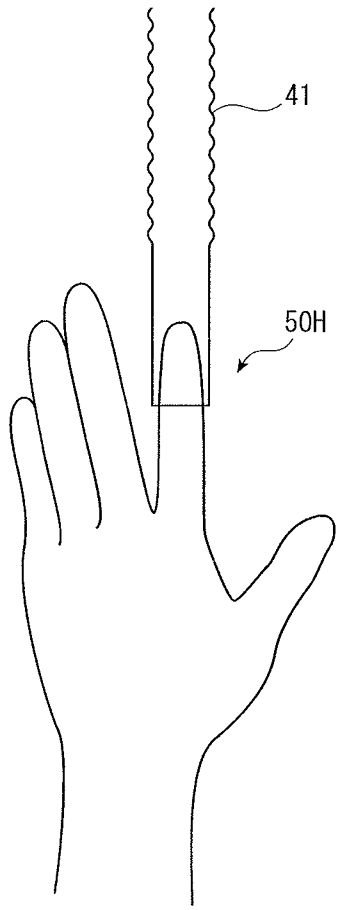
FIG. 11 Atypical view showing a configuration example (No. 4) of the living body cover in the gas mist pressure bathing system in dependence on the first embodiment of the invention.

As a more simple living body cover 50, as shown in FIG. 11, the living body (herein, the tip of a finger) is attached at the front end of the gas mist supply pipe 41, and the gas mist supply pipe 41 may be used itself as a living body cover 50H. In such a case, the gas mist supply pipe 41 is preferably composed with an elastic raw material.

By the way, since the living body cover 50H shown in FIG. 11 limits attachable parts of the living body, such a living body cover 50I may be used which is composed of a connection part 56 with the gas mist supply pipe 41 and an elastic tubular member 57 which is larger in diameter than the gas mist supply pipe 41. When using this living body cover 50I, the connection part 56 is connected to the gas mist supply pipe 41 at its front, and attached by inserting the living body (herein, the tips of the finger and of a foot) into the elastic tubular member 57. This living body cover 50I has an advantage of being very simple in attaching to the living body. Further, this is also useful when there is a part desiring to contact the gas mist particularly by concentration.

Figure 12B:
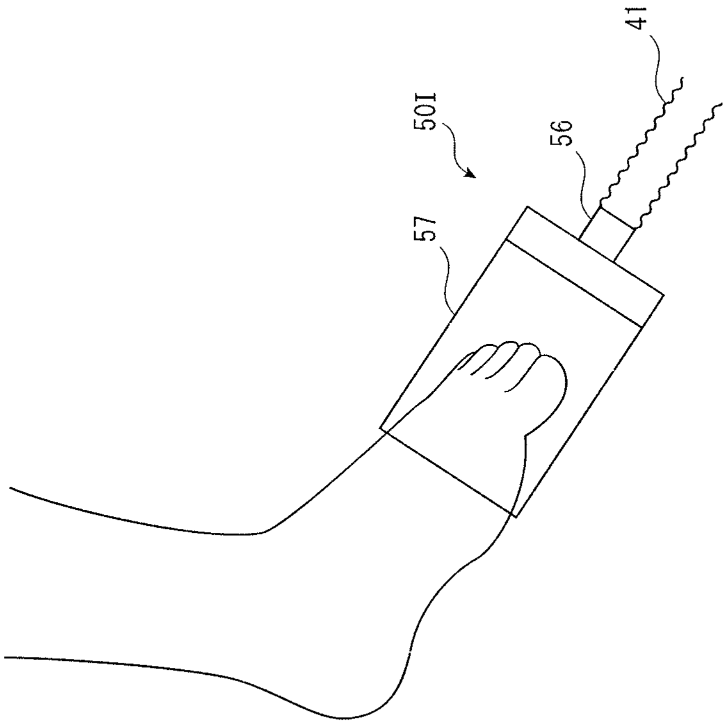
FIGS. 12A-12B Typical views showing configuration examples (No. 5) of the living body cover in the gas mist pressure bathing system in dependence on the first embodiment of the invention.
Figure 12A:
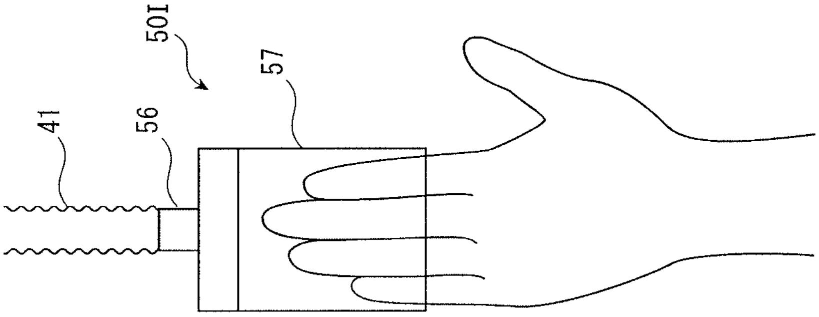
Figure 13:
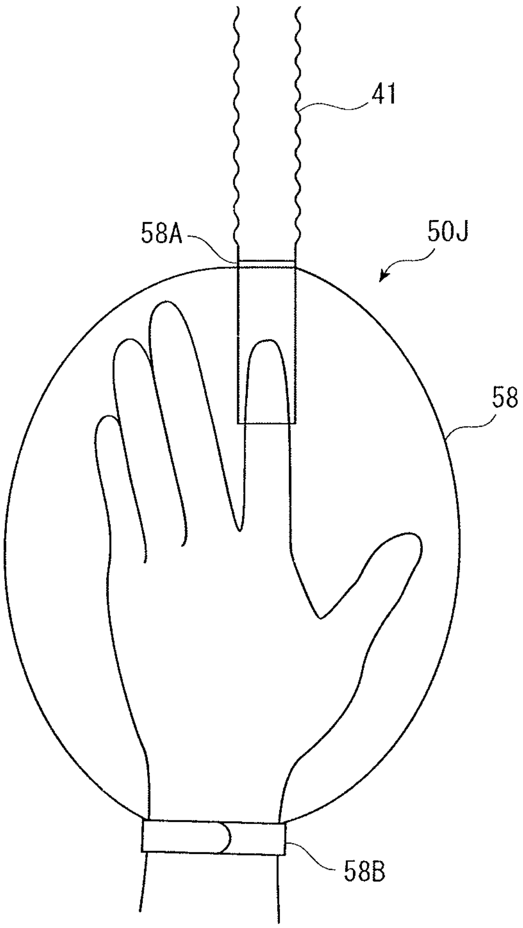
FIG. 13 Atypical view showing a configuration example (No. 6) of the living body cover in the gas mist pressure bathing system in dependence on the first embodiment of the invention.
Figure 14B:
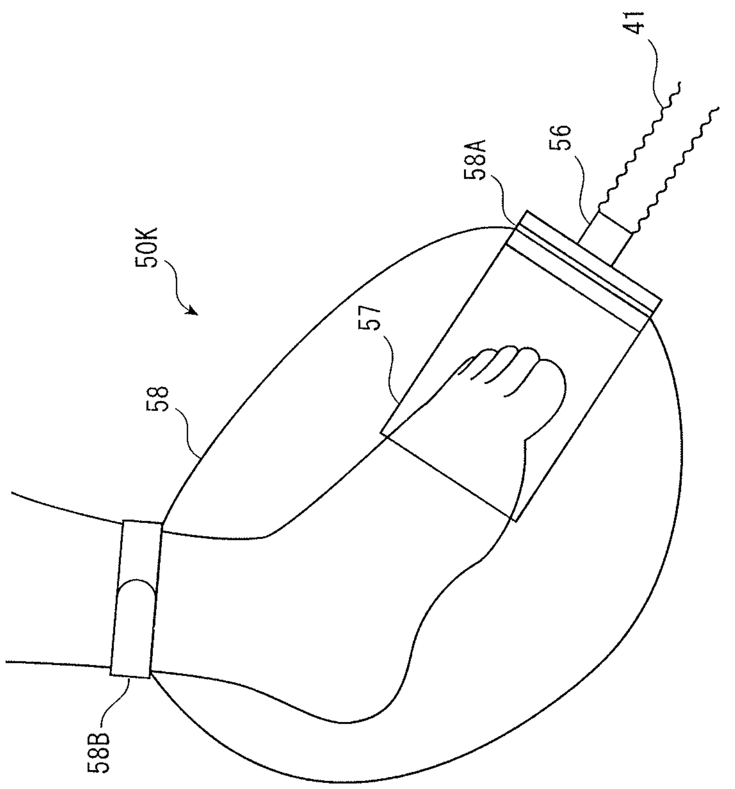
FIGS. 14A-14B Typical views showing configuration examples (No. 7) of the living body cover in the gas mist pressure bathing system in dependence on the first embodiment of the invention.
Figure 14A:
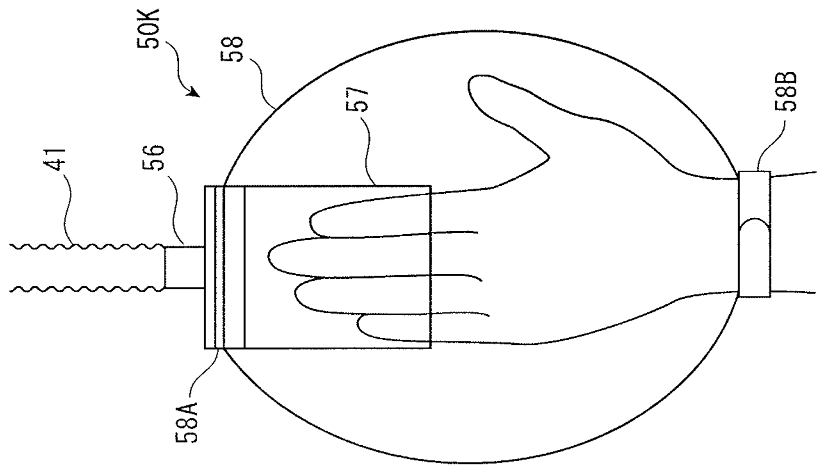

Besides the living body covers 50H, 50I shown in FIGS. 11 and 12, it is also sufficient to furnish infolding members 58 as shown in FIGS. 13 and 14 to make living body covers 50J, 50K. One end 58A of the infolding members 58 is attached to the gas mist supply pipe 41 or to the connection part 56. Further, the other end 58B is attached to the living body (herein, fingers, wrist and ankle). The respective ends 58A, 58B of the infolding members 58 are arranged with elastic face fasteners to be easily attached to or detached from the ends 58A, 58B.

In regard to the living body cover 50, various shapes may be assumed other than the examples shown in FIGS. 8 to 14. In particular, since this invention can be applied to not only the human living body, but also to general kinds of animals, the living body cover 50 adopts shapes in view of the using objects and using parts. In sum, if enabling to form spaces for sealing the skins and the mucous membranes of the living body and to form inside spaces for sealing the gas mist, any shapes are sufficient. Although omitting illustrations here, it is suitable to furnish air ports for discharging the gas mist in the living body cover 50 or controlling pressurization.

The gas mist pressure bathing contacts the gas mist to the skin and mucous membrane of the living body at pressure of more than the predetermined value, and such pressurization heightens the effects by performing as pulsing at predetermined intervals, and therefore it is sufficient that the control device 60 supplies the gas mist into the living body cover 50 intermittently at fixed rhythm. As to the interval pressurization at such a case, if synchronizing with pulsations, the effects are more heightened.

Figure 15:
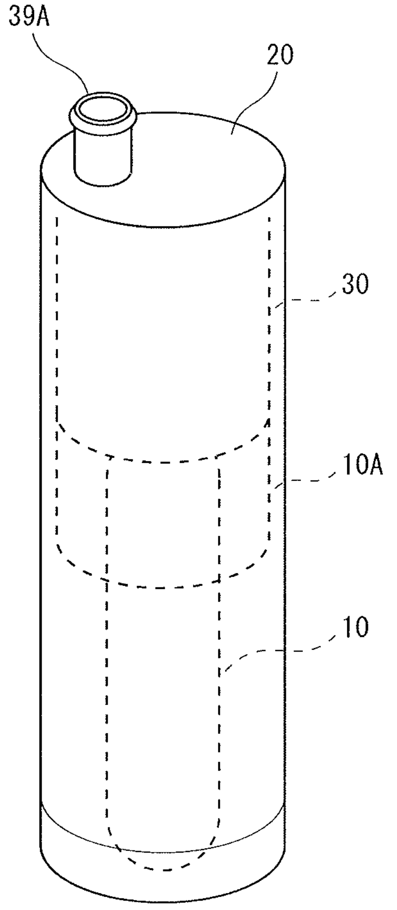
FIG. 15 A typical view showing a general appearance of a case when housing the gas supply means and the gas mist generator of the invention therein.
Figure 16A:
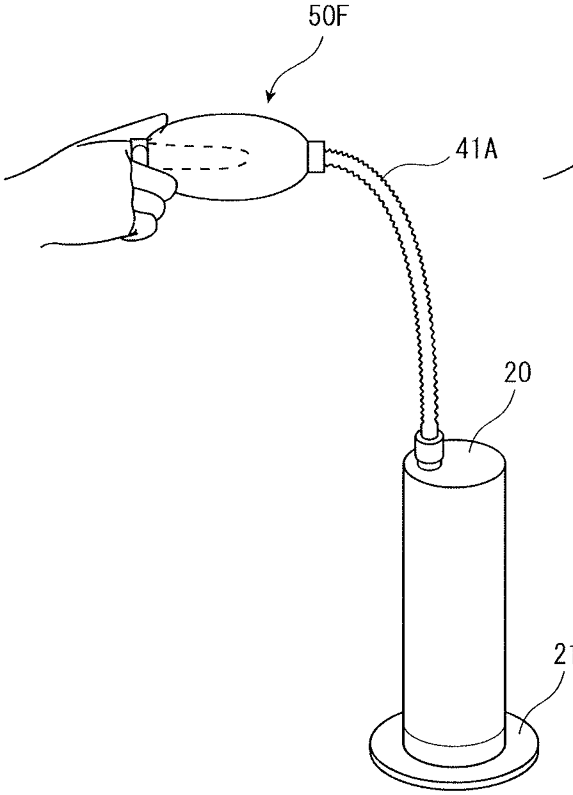
FIGS. 16A-16C Typical views showing examples of conditions using the case shown in FIG. 15.
Figure 16C:
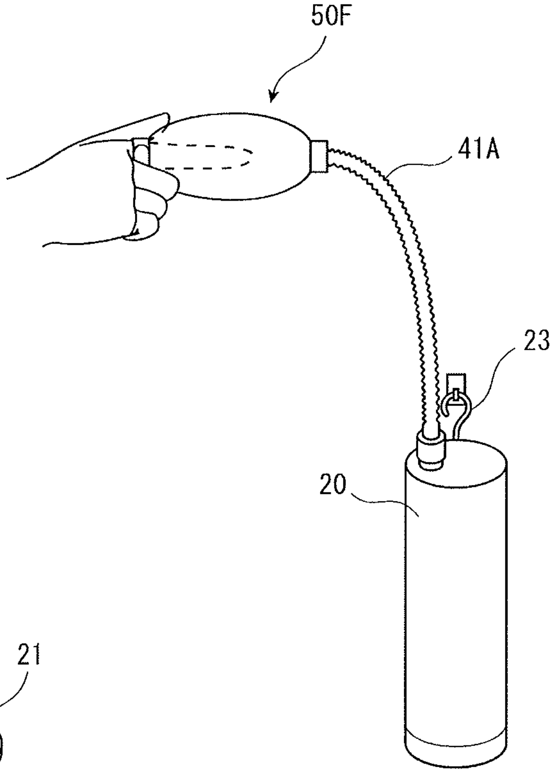
Figure 16B:
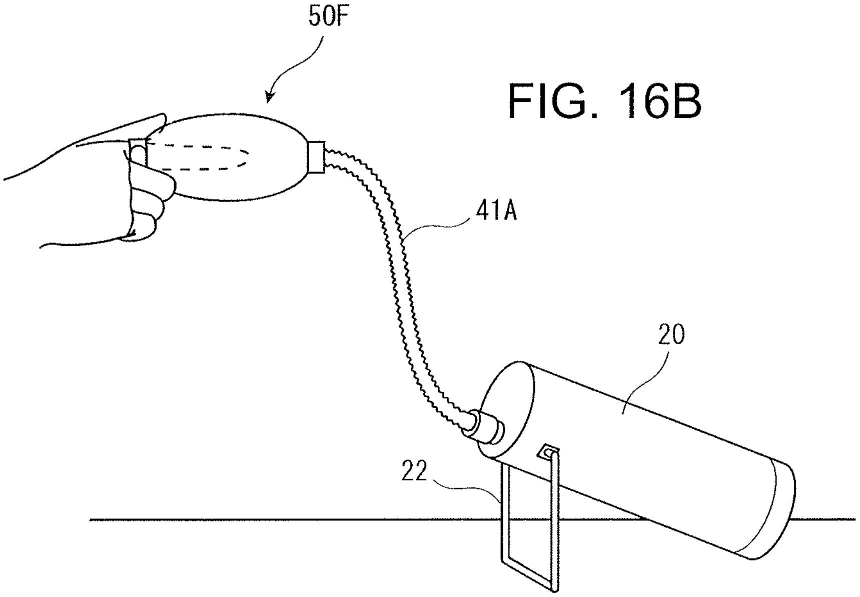

If a simple means like the cartridge system gas bomb is used as the gas supply means 10, it is possible to use the gas supply means 10 and the gas mist generator 30 (more preferably, the control device 60) under a compact condition of containing them in the case 20 as showing in FIG. 15. Herein, the gas supply means 10 has a regulator 10A. FIGS. 16A to 16C show examples of using conditions. As showing in FIGS. 16A to 16C, the cases 20 have stands 21, 22 or a hook 23 to stand upright, so that the gas mist generator 30 is used as standing as possible. By such manners, the liquefied gas mist is easily recovered.

Second Embodiment

Figure 17:
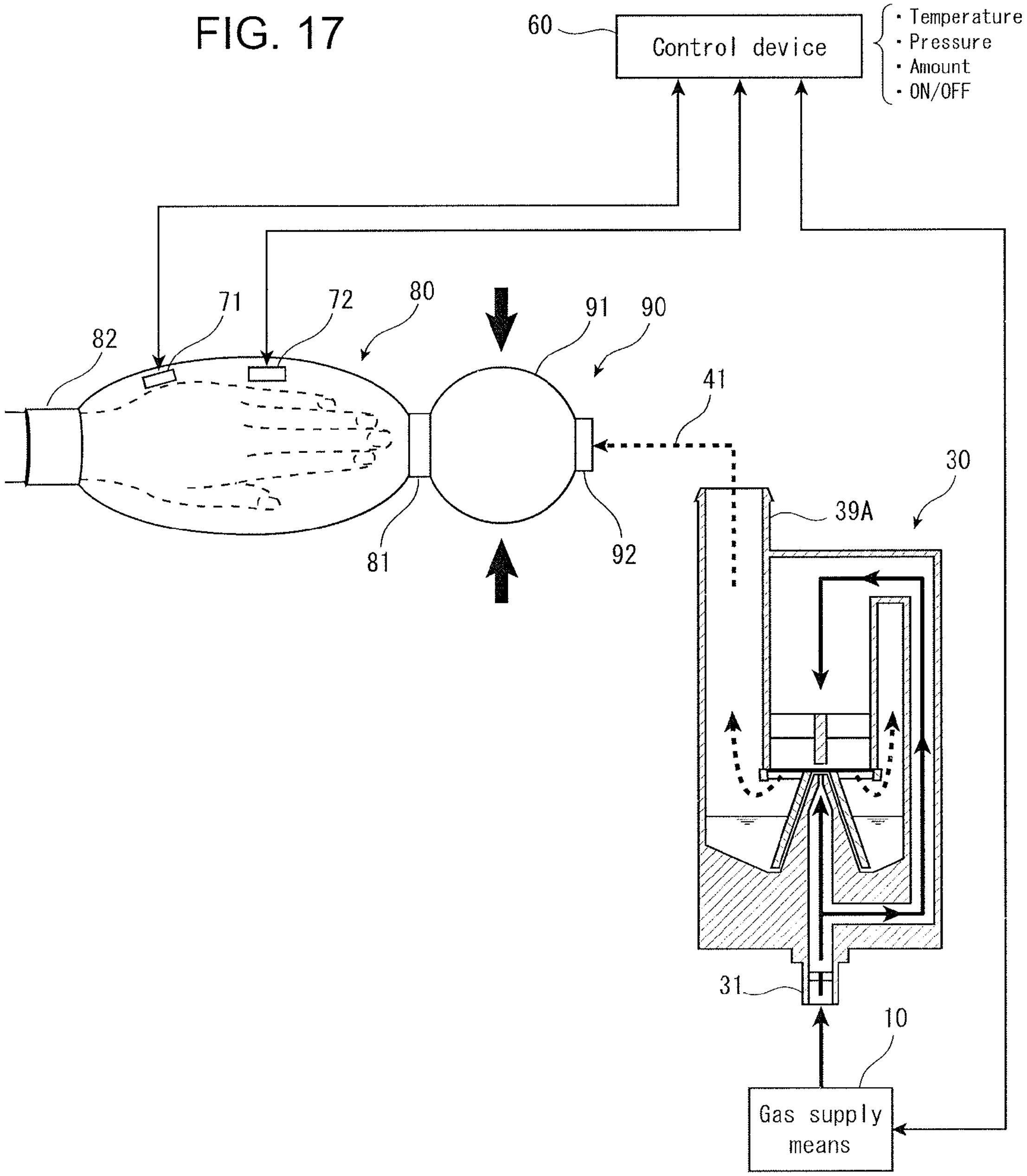
FIG. 17 A generally schematic view of the gas mist pressure bathing system in dependence on the second embodiment of the invention.

FIG. 17 is the generally schematic view of the gas mist pressure bathing system in dependence on a second embodiment of this invention. This embodiment will explain the gas mist pressure bathing system further having a pressurizing means for making pressurization easy within the living body cover. As to the same parts as those of the first embodiment shown in FIG. 1, the same numerals will be given, and detailed explanation will be omitted.

As shown in FIG. 17, the gas mist pressure bathing system of this embodiment has a living body cover 80 forming a space into which the gas mist is sealed inside, and a pressurizing means 90 communicating with the living body cover 80 for carrying out pressurization in the living body cover 80.

The living body cover 80 has almost the same structure of the living body cover 50 shown in the first embodiment, and has a supply port 81 of the gas mist and gas and a stopper gas 82, providing that the supply port 81 is connected to the pressurizing means 90 in the present embodiment. By the way, as an example herein, illustrated is the living body cover 80 having a shape of covering a hand of the living body.

The pressurizing means 90 pressurizes the inside of the living body cover 80, and therefore has a hollow gas storage 91 communicating with the living body cover 80. The gas storage 91 is composed of a soft material having pressure resistance, non-air permeability and non-moisture permeability. The pressurizing means 90 is connected to the supply port 81 of the living body cover 80, and has a supply port 92, from which the gas mist and gas are supplied into the gas storage 91. In addition, the supply port 92 of the pressurizing means 90 is also provided inside with the check valve for checking back-flow of the gas mist and gas.

For pressurizing the living body cover 80 by the pressurizing means 90, the gas mist and gas are stored in the gas storage 91 under a condition where the gas mist is moderately stored within the living body cover 80. If pressurizing the gas storage 91 in a manner as crashing as shown with arrows in FIG. 17, the gas mist and gas in the gas storage 91 are discharged into the living body cover 80, so that the inside of the living body cover 80 can be pressurized.

The pressurizing means 90 is enough with a structure of manually pushing, or sufficient to mechanically control by the control device 60 using a driving device. As mentioned above, since pressurization in the gas mist pressure bath heightens effects by pulse-like performance at a determined interval, it is effective to intermittently push the pressurizing means 90 at constant rhythm.

When taking the gas mist pressure bathing by use of the gas mist pressure bathing system of this embodiment, at first, the sealed gas mist generator 30 is opened to connect the gas supply means 10. The living body cover 80 is fixed to the living body (herein, the hand) and sealed. Supply of gas starts from the gas supply means 10 into the gas mist generator 30 for generating the gas mist. During this period, the control device 60 controls supply pressure, amount of the liquid and gas, and temperature.

The generated gas mist is mixed with gas from the diverging portion 32, and discharged from the gas mist discharge part 39 into the pressurizing means 90 and the living body cover 80 through gas mist supply pipe 41 from the gas mist discharge port 39A. The control device 60 controls the respective means from measuring values of the temperature gauge 72, such that the inside of the living body cover 80 is maintained under the optimum heated condition (for example, around 38° C.). When the gas mist and gas of the optimum amount are stored in the living body cover 80 and the pressurizing means 90, the pressurizing means 90 is pushed to moderately pressurize (around 1.01 to 1.4 air pressure) the living body cover 80 for taking the gas mist pressure bathing.

As having mentioned in the first embodiment, various shapes of the living body cover 80 may be employed, since they are applied to many parts of the living body, providing that in the present embodiment, the living body cover 80 must have a size easily pressurized by the pressuring means 90. For example, when manually pressurizing the pressuring means 90, the pressuring means 90 must have such a size grasped by man's both hands, and the living body cover 80 pressurized with the pressuring means 90 is also limited in size, accordingly. Further, even if, in a case of pressurizing with such as a driving device, the pressuring means 90 and also a means pressurizing this means are desirably compact not to actually keep wide places, therefore, the present embodiment is applicable to the living body cover 80 which is comparatively compact (covering local parts of the living body).

FIGS. 18 and 19 show the examples of shapes of the living body cover 80 to which the present embodiment is easily applied as well as those of the pressuring means 90 connected thereto. FIG. 18A is a living body cover 80A for one-side lower extremity (lower part under a knee) of the living body. The living body cover 80A has a supply port 81A for introducing inside the gas mist and gas and the stopper 82A at its open. The supply port 81A is connected to a pressuring means 90A. The pressuring means 90A has a gas storage 91A and a supply port 92A. FIG. 18B is a living body cover 80B for feet of the living body. The living body cover 80B has a supply port 81B for introducing inside the gas mist and gas and a stopper 82B at its opening part. The supply port 81B is connected with a pressurizing means 90B. The pressurizing means 90B has a gas storage 91B and a supply port 92B. FIG. 18C is a living body cover 80C for a forearm of the living body. The living body cover 80C has a supply port 81C for introducing inside the gas mist and gas and a stopper 82C at its opening part. The supply port 81C is connected with a pressurizing means 90C. The pressurizing means 90C has a gas storage 91B and a supply port 92C.

Figure 19A:
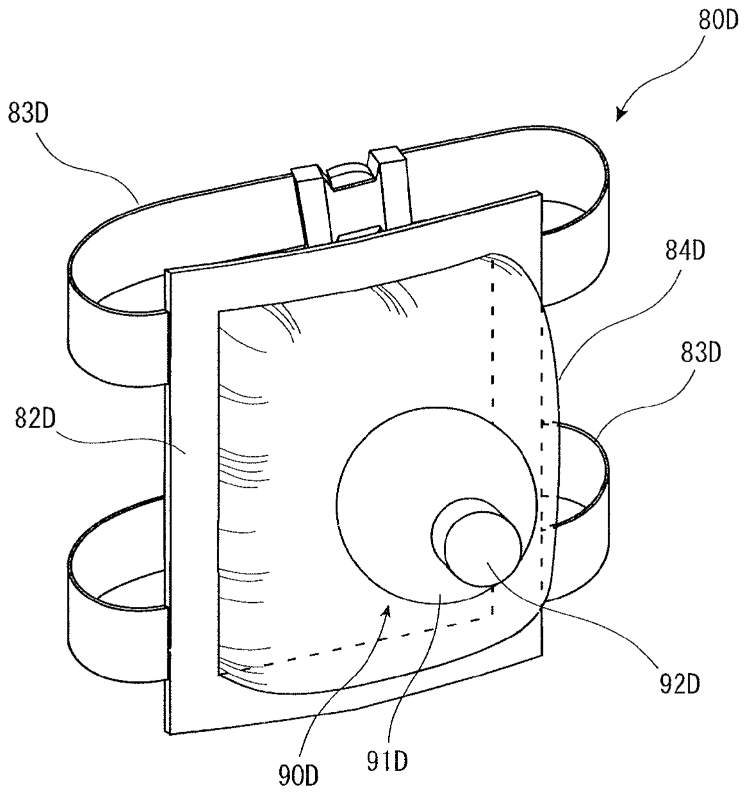
FIGS. 19A-19B Typical views showing a configuration example (No. 2) of the living body cover in the gas mist pressure bathing system in dependence on the second embodiment of the invention.
Figure 19B:
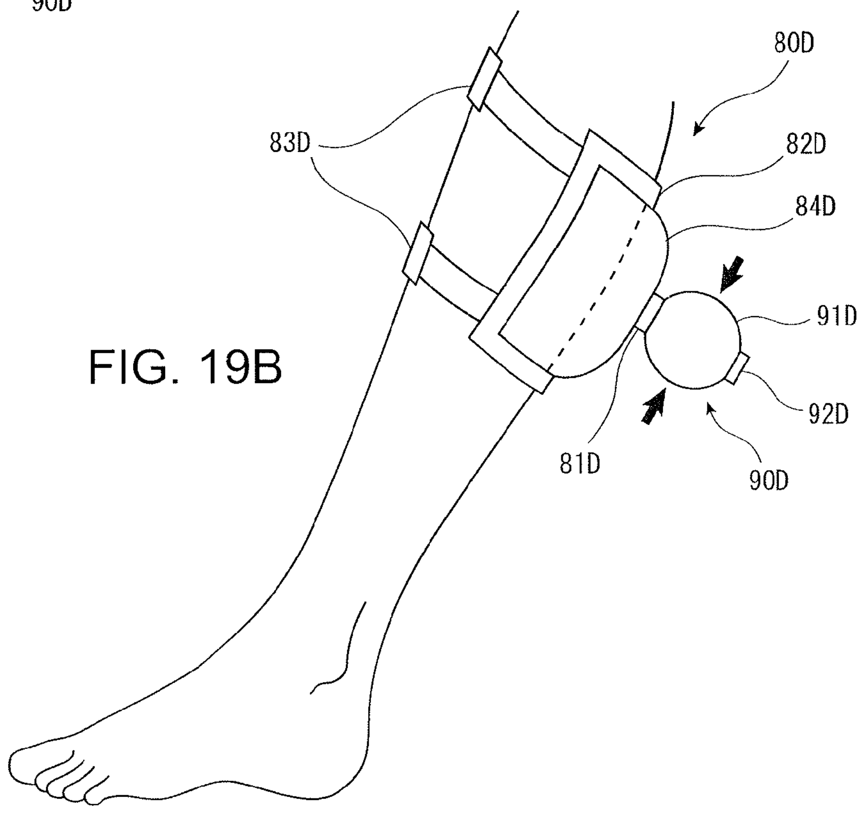

FIGS. 19A and 19B show an example of a patch shaped living body cover 80D. FIG. 19A is a view showing the outline of the patch shaped living body cover 80D, and FIG. 19B is a view showing an external appearance when attaching the patch shaped living body cover 80D to the living body (herein, the lower extremity). The living body cover 80D is composed of a cover part 84D for covering the skin and mucous membrane of the living body, a stopper 82D provided at the margin of the cover part 84D and directly attached to the skin and mucous membrane of the living body, fasteners 83D made of belts or strings for fastening the cover part 84D to the living body, and a supply port 81D for supplying the gas mist and gas into the space defined by the cover part 84D and the stopper 82D. The supply port 81D is connected with the pressurizing means 90D. The pressurizing means 90D has the gas storage 91D and the supply port 92D.

Incidentally, although having omitted shown here, preferably there is provided an discharge port for discharging the gas mist and gas existing in the living body cover 80 or for adjusting pressure.

In the above embodiment, the pressurizing means 90 is composed of a hollow gas storage 91 communicating to the living body cover 80, and any members are sufficient if those can enable to conveniently pressurize the living body cover 80 such as a member compressing to crash the living body cover 80 from an outer periphery.

Third Embodiment

Figure 20:
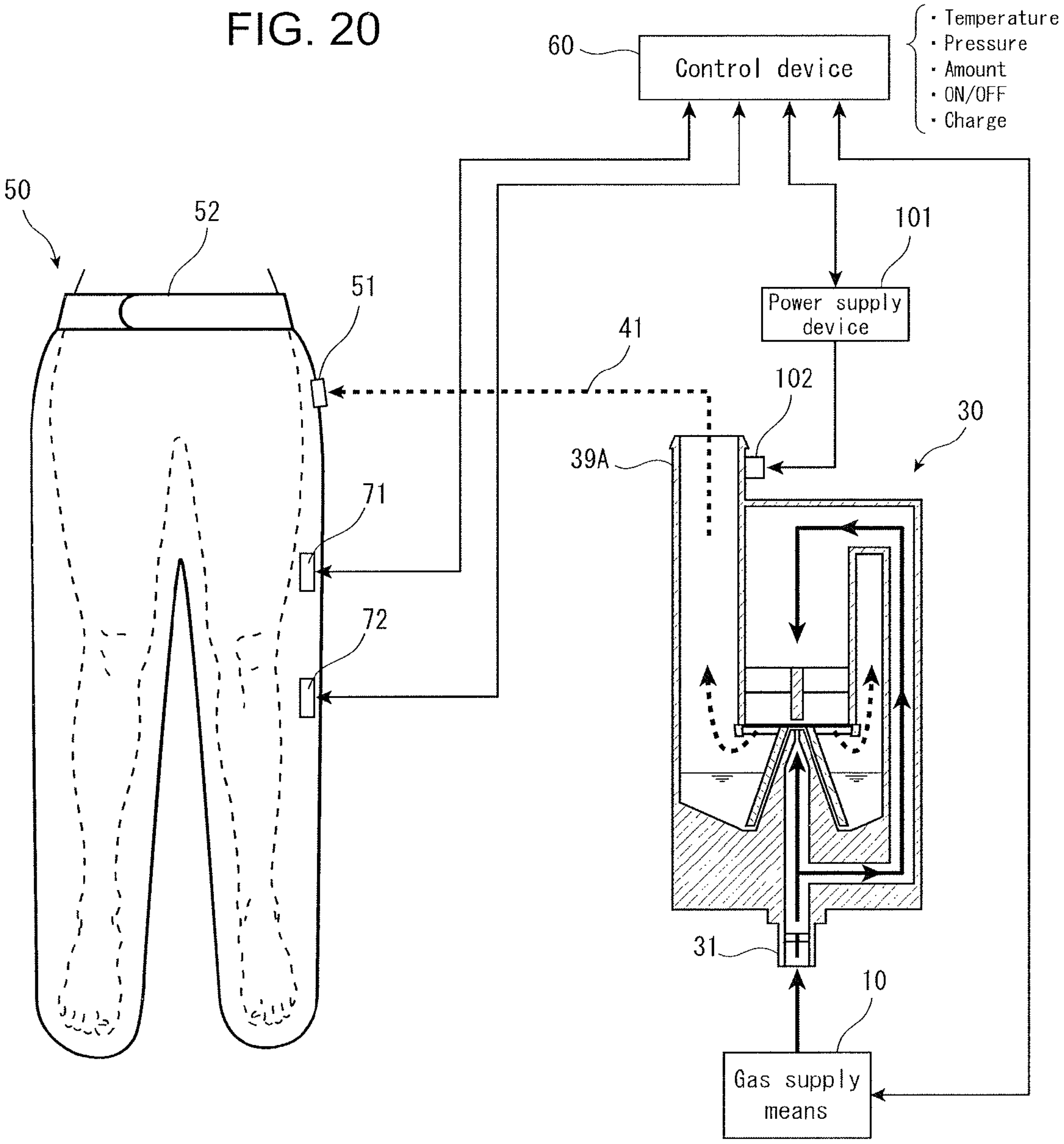
FIG. 20 A generally schematic view of the gas mist pressure bathing system in dependence on a third embodiment of the invention.

FIG. 20 is the generally schematic view of the gas mist pressure bathing system depending on a third embodiment of this invention. This embodiment will explain the gas mist pressure bathing system which further has a means for electrically charging a generated mist. As to the same parts as those of the first embodiment shown in FIG. 1, the same numerals will be given, and detailed explanation will be omitted.

As shown in FIG. 20, a gas mist pressure bathing system of this embodiment is arranged with an electrode 102 in the vicinity of the exit of a gas mist discharge port 39A of the gas mist generator 30. The electrode 102 is connected to a source device 101, and a control device 60 sets voltage values and performs on-off control.

The electrode 102 supplies an electric charge (minus charge is desirable) when discharging the mist generated by the gas mist generator 30. Thereby, the mist is made charged so that adhesion to a charged material can be heightened. That is, if heightening adhesion to the skin and the mucous membrane of the living body, an effect of increasing absorption rate of gas by the gas mist pressure bathing is furthermore heightened, and if the gas mist contains the above mentioned medicines, penetration into the skin and the mucous membrane can be more accelerated.

When carrying out the gas mist pressure bathing by using the gas mist pressure bathing system of the present embodiment, at first, the sealed gas mist generator 30 is opened, and connected to the gas supply means 10. The living body cover 50 is fixedly secured to the living body (herein, the lower extremity) and closed. The gas supply starts from the gas supply means 10 to the gas mist generator 30 for generating the gas mist. During this period, the control device 60 controls supply pressure, amount of the liquid, gas or temperature. Further, the control device 60 turns on the electric power device 101 and gives an electric charge from the electrode 102 to the mist.

The generated gas mist is mixed with gas from the diverging portion 32, and is discharged to the living body cover 50 from the gas mist discharge port 39A through the gas mist supply pipe 41. The control device 60 controls each of the means from measuring values of the manometer 71 and the temperature gauge 72 such that the inside of the living body cover 50 becomes the optimum pressurized and heated conditions (around 1.01 to 1.4 air pressure, and around 38° C.), and under this condition the gas mist pressure bathing is carried out.

Having composed the structure as mentioned above, according to the gas mist pressure bathing system, the gas inlet of heightening supply pressure of the gas mist is formed integrally with the gas mist generator, so that the gas mist generation means simplifies the structure, reduces labor during working, and lowers production cost. Further, gas leakage can be avoided.

The above references have explained the embodiments of the invention, but are not limited thereto, and so far as not deviating from the subject matter of the invention, various kinds of embodiments are, of course, available.

INDUSTRIAL APPLICABILITY

This invention relates to the gas mist pressure bathing system for improving absorption efficiency of gas into the skin or the mucous membrane of the living body, in which the mist is prepared by pulverizing and dissolving the liquid of oxygen and carbon dioxide, or the liquid of the mixed gas of oxygen and carbon dioxide, and the mist is caused to directly contact the skin or mucous membrane of the living body at pressure of not less than a predetermined value, and thus the present invention accompanies industrial applicability.

EXPLANATION OF THE REFERENCE NUMERALS AND SIGNS

10: Gas supply means
20: case
21, 22: stand
23: hook
30: gas mist generator
31: connecting part
32: diverging portion
33: liquid storage
34: nozzle
34A: front point open of the nozzle
35: liquid suction pipe-forming member
35A: liquid suction pipe
35B: front point of the suction pipe
36: baffle
36A: baffle supporter
37: confluent part
38: gas inlet
39: gas mist discharge part
39A: gas mist discharge port
41: gas mist supply pipe
41A: cornice shaped pipe
42: groove
50, 50A, 50B, 50C, 50D, 50E, 50F, 50G, 80, 80A, 80B, 80C, 80D: living body cover
51, 51A, 51B, 51C, 51D, 51E, 51F, 51G, 81, 81A, 81B, 81C, 81D: supply port
52, 52A, 52B, 52C, 52D, 52E, 52F, 52G, 82, 82A, 82B, 82C, 82D: stopper
53G, 53D: fixing part
54G, 54D: cover
60: control device
71: manometer
72: temperature gauge
90, 90A, 90B, 90C, 90D: pressuring means
91, 91A, 91B, 91C, 901: gas storage
92, 92A, 92B, 92C, 92D: supply port
101: power supply device
102: electrode

The invention claimed is:

1. A gas mist pressure bathing system, which causes a mist (called as "gas mist" hereafter) to contact the skin or the mucous membrane of a living body, the mist having been prepared by pulverizing and dissolving carbon dioxide or oxygen and liquid, or a mixed gas (called as "gas" hereafter) of carbon dioxide and oxygen and liquid of concentration being not less than predetermined value, comprising a gas supply means for supplying the above gas, a gas mist generation means for generating the gas mist of the gas supplied from the gas supply means and the liquid stored inside, and supplying the gas mist under a condition of mixing with the above gas, and a living body cover member for covering the skin and the mucous membrane of the living body and formed with a space for sealing inside the gas mist and gas supplied from the gas mist generation means, wherein the above mentioned gas mist generation means is integrally provided with a connection part to the gas supply means;

a diverging portion of branching a gas flow from the connection part;

a liquid storage of storing the liquid;

a nozzle of discharging one-side gas flow branched by the diverging portion and a liquid suction pipe of sending the liquid to a front end of the nozzle;

a collision member of generating the gas mist by colliding the liquid blown up by the gas flow discharged from the nozzle with this collision member;

a confluent part of joining the generated gas mist with the gas from an upward side;

a gas inlet of leading the other-side gas flow branched by the diverging portion until the confluent part; and a gas mist discharge part of collecting and discharging the generated gas mist and gas.

2. The gas mist pressure bathing system as set forth in claim 1, wherein, in the gas mist generation means, at least the liquid storage is made removable and exchangeable with another liquid storage.

3. The gas mist pressure bathing system as set forth in claim 1, further provided with sensors for detecting measured values of air pressure, temperature, concentrations of oxygen and carbon dioxide, and moisture within the living body cover member and control means for controlling the interior of the living body cover member based on the measured values of the sensors to be within ranges of the set values having been in advance determined.

4. The gas mist pressure bathing system as set forth in claim 1, further provided with a pressurization means for pressurizing the interior of the living body cover member.

5. The gas mist pressure bathing system as set forth in claim 4, wherein the above mentioned pressurization means communicates with the living body cover member, and consists of a hollow gas storage enabling to discharge the gas mist into the living body cover member.

6. The gas mist pressure bathing system as set forth in claim 3, wherein the above mentioned control means supplies the gas mist intermittently into the living body cover member, so that the living body cover member may be effected with interval pressurization.

7. The gas mist pressure bathing system as set forth in claim 5, wherein the pressurization member intermittently discharges the gas mist into the living body cover member to carry out the interval pressurization on the living body cover member.

8. The gas mist pressure bathing system as set forth in claim 1, wherein the above mentioned liquid is any one or plural combination of water, ionic water, ozone water, physiological salt solution, purified water, or sterilized and purified water.

9. The gas mist pressure bathing system as set forth in claim 8, wherein the above mentioned liquid further contains any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, citric acid, ethanol, chlorhexidine gluconate, amphoteric surface active agent, benzalkonium chloride, alkyl diamino etherglycine acetate, sodium hypochlorite, peracetic acid, sodium sesqui-carbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

10. The gas mist pressure bathing system as set forth in claim 1, wherein a size of the mist supplied from the gas mist generation means into the living body cover member is not larger than 10 μm.

11. The gas mist pressure bathing system as set forth in claim 1, wherein the control means holds pressure at 1.01 to 1.4 air pressure within the living body cover member when taking the gas mist pressure bathing.

12. The gas mist pressure bathing system as set forth in claim 1, wherein an electric charge giving means is provided for giving an electric charge to the mist supplied by the gas mist generation means.

13. The gas mist pressure bathing system as set forth in claim 12, wherein the electric charge is preferably minus.

14. The gas mist pressure bathing system as set forth claim 1, wherein the gas mist generation means has a gas mist supply pipe for supplying the gas mist and gas into the living body cover, and this gas mist supply pipe is furnished with a filter for removing liquid drops attaching to the inside of the pipe.

15. The gas mist pressure bathing system as set forth in claim 1, wherein the gas mist generation means has a gas mist supply pipe for supplying the gas mist and gas into the living body cover, and the gas mist supply pipe is composed of a cornice shaped pipe over a whole or at one part of the gas mist supply pipe.

16. The gas mist pressure bathing system as set forth in claim 15, wherein the cornice shaped pipe is formed inside with a groove in an axial direction of the pipe.

17. The gas mist pressure bathing system as set forth in claim 1, wherein the gas mist generation means has a gas mist supply pipe for supplying the gas mist and gas into the living body cover, and this gas mist supply pipe is provided with a check valve.

18. The gas mist pressure bathing system as set forth in claim 1, wherein the living body cover member is furnished with the check valve at the gas mist supply port.

19. The gas mist pressure bathing system as set forth in claim 1, wherein the control means stops gas supply from the gas supply means when the pressure value becomes more than the predetermined value.

20. The gas mist pressure bathing system as set forth in claim 1, wherein the gas mist generation means is in advance sterilized.

* * * * *